United States Patent
Ishikawa et al.

(10) Patent No.: US 9,616,612 B2
(45) Date of Patent: Apr. 11, 2017

(54) APPARATUS FOR PRODUCING A STRETCHABLE SHEET

(71) Applicant: Uni-Charm Corporation, Shikokuchuo-shi, Ehime (JP)

(72) Inventors: Shinichi Ishikawa, Kanonji (JP); Jun Okuda, Kanonji (JP); Taishi Nakamura, Kanonji (JP); Akihisa Shiomi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/683,116

(22) Filed: Apr. 9, 2015

(65) Prior Publication Data

US 2015/0210000 A1    Jul. 30, 2015

Related U.S. Application Data

(62) Division of application No. 13/577,030, filed as application No. PCT/JP2011/054738 on Mar. 2, 2011, now Pat. No. 9,296,151.

(30) Foreign Application Priority Data

Mar. 10, 2010   (JP) ................................ 2010-053603

(51) Int. Cl.
*B29C 55/18*   (2006.01)
*D06C 3/06*   (2006.01)
(Continued)

(52) U.S. Cl.
CPC ........ *B29C 55/18* (2013.01); *A61F 13/15593* (2013.01); *A61F 13/56* (2013.01);
(Continued)

(58) Field of Classification Search
CPC ............. B29C 55/18; D06C 3/06; D04H 3/16
(Continued)

(56) References Cited

U.S. PATENT DOCUMENTS 4,614,632 A * 9/1986 Kezuka ................... B29C 51/08
264/280
5,167,897 A * 12/1992 Weber ............... A61F 13/15593
264/101
(Continued)

FOREIGN PATENT DOCUMENTS

CN            1406568 A      4/2003
CN          101166858 A      4/2008
(Continued)

OTHER PUBLICATIONS

International Search Report for PCT/JP2011/054738, dated Apr. 12, 2011.
(Continued)

*Primary Examiner* — Nahida Sultana
(74) *Attorney, Agent, or Firm* — Hauptman Ham, LLP

(57) ABSTRACT

An apparatus for producing a stretchable sheet includes a pair of gear rolls each having a plurality of teeth arranged on a circumference thereof. The apparatus is configured to draw a raw sheet by passing the raw sheet through a gap between the pair of gear rolls. The raw sheet contains a plurality of types of fibers, and has a plurality of recessed sections formed by pressing. The recessed sections are formed collinearly at least along the drawing direction at a predetermined formation pitch in the drawing direction. An arrangement pitch of the teeth in the drawing direction is greater than the formation pitch and smaller than twice the formation pitch.

10 Claims, 11 Drawing Sheets

(51) Int. Cl.
  *A61F 13/56* (2006.01)
  *A61F 13/15* (2006.01)
  *D04H 3/16* (2006.01)
  B29L 31/48 (2006.01)

(52) U.S. Cl.
  CPC ............... *D04H 3/16* (2013.01); *D06C 3/06*
  (2013.01); *B29L 2031/4878* (2013.01)

(58) Field of Classification Search
  USPC .... 425/363; 264/290.2, 286, 288.4; 156/205
  See application file for complete search history.

(56) References Cited

U.S. PATENT DOCUMENTS

| | | | |
|---|---|---|---|
| 6,039,555 A | | 3/2000 | Tsuji et al. |
| 7,468,114 B2* | | 12/2008 | Sato .................. A61F 13/15707 |
| | | | 156/209 |
| 7,754,050 B2* | | 7/2010 | Redd ......................... B31F 1/07 |
| | | | 162/117 |
| 8,012,388 B2 | | 9/2011 | Akaki et al. |
| 8,945,452 B2 | | 2/2015 | Morita et al. |
| 8,974,890 B2 | | 3/2015 | Mitsuno |
| 9,296,151 B2* | | 3/2016 | Ishikawa ................. D06C 3/06 |
| 2003/0028165 A1 | | 2/2003 | Curro et al. |
| 2004/0140047 A1 | | 7/2004 | Sato et al. |
| 2007/0029073 A1* | | 2/2007 | Teshima ............... B21D 31/046 |
| | | | 165/109.1 |
| 2007/0207050 A1* | | 9/2007 | Ohmi .................... F04C 18/084 |
| | | | 418/201.1 |
| 2008/0271556 A1* | | 11/2008 | Imamura ........... F16H 57/02004 |
| | | | 74/412 R |
| 2009/0035527 A1 | | 2/2009 | Kobayashi et al. |
| 2009/0133180 A1 | | 5/2009 | Morita et al. |
| 2009/0286639 A1* | | 11/2009 | Sakura ..................... F16H 55/08 |
| | | | 474/152 |
| 2009/0308524 A1 | | 12/2009 | Gunji et al. |
| 2010/0065984 A1* | | 3/2010 | Akaki ..................... B29C 55/18 |
| | | | 264/288.4 |
| 2011/0042849 A1 | | 2/2011 | Akaki et al. |
| 2013/0273322 A1* | | 10/2013 | Boegli ...................... B31F 1/07 |
| | | | 428/156 |

FOREIGN PATENT DOCUMENTS

| | | |
|---|---|---|
| CN | 101310066 A | 11/2008 |
| CN | 101535549 A | 9/2009 |
| EP | 1876275 A1 | 1/2008 |
| EP | 1956131 A1 | 8/2008 |
| JP | 200881849 A | 4/2008 |
| JP | 2009228145 A | 10/2009 |
| WO | 0231245 A2 | 4/2002 |
| WO | 0231245 A3 | 4/2002 |
| WO | 2006115259 A1 | 11/2006 |
| WO | 2007063661 A1 | 6/2007 |
| WO | 2008/078533 A1 | 7/2008 |
| WO | 2009116440 A1 | 9/2009 |

OTHER PUBLICATIONS

Extended European Search Report issued Oct. 7, 2013, corresponds to European Patent application No. 11753238.2.
Office Action mailed Jan. 26, 2014, corresponds to Chinese patent application No. 201180013048.0.
Office Action issued May 30, 2014, corresponds to European patent application No. 11753238.2.
Office Action mailed Oct. 17, 2014, corresponding to Chinese patent application No. 201180013048.0.
Office Action mailed Jul. 15, 2015, corresponding to U.S. Appl. No. 13/577,030.
Office Action dated Nov. 6, 2015, corresponding to European Patent Application No. 11753238.2.

* cited by examiner

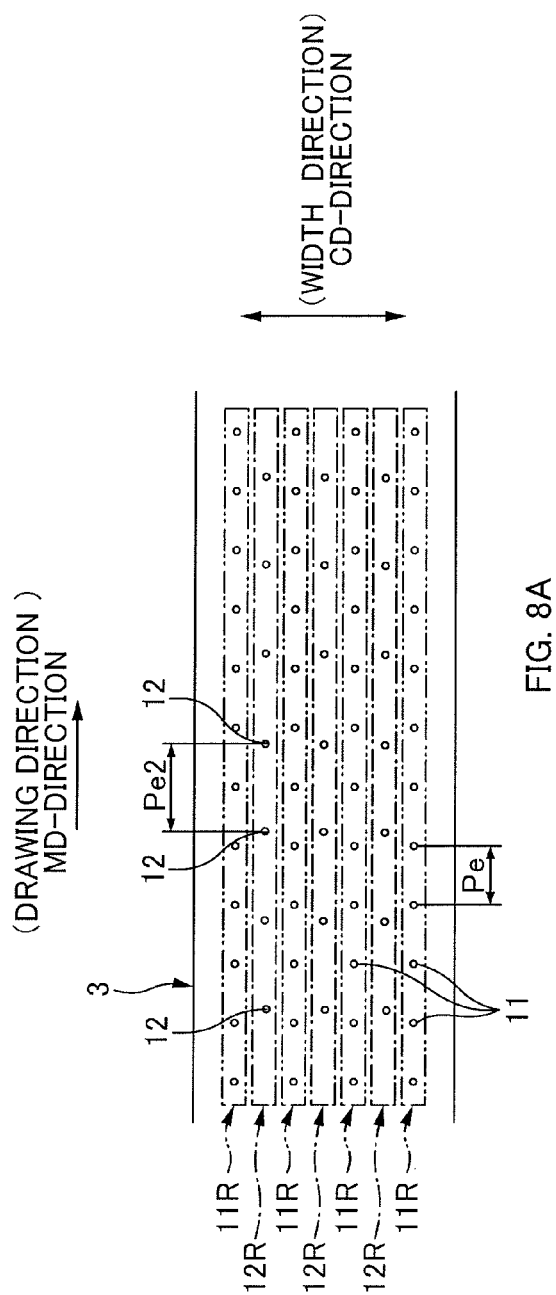
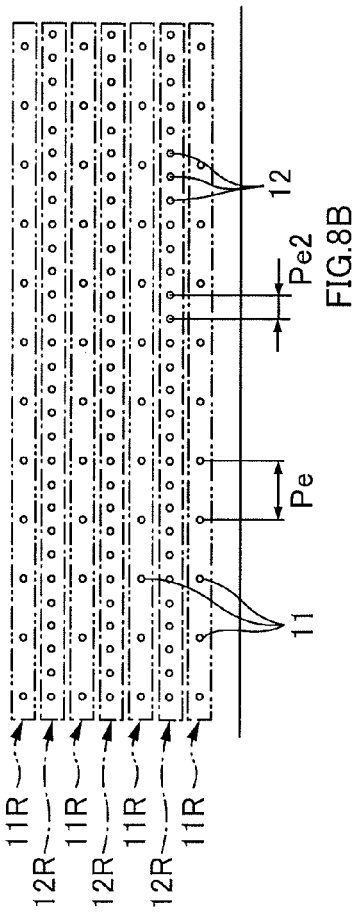
FIG. 8A
FIG. 8B

APPARATUS FOR PRODUCING A STRETCHABLE SHEET

RELATED APPLICATIONS

The present invention is a divisional of U.S. patent application Ser. No. 13/577,030 filed Oct. 22, 2012 which is a National Phase of International Application No. PCT/JP2011/054738, filed Mar. 2, 2011, and claims priority from Japanese Application Number 2010-053603, filed Mar. 10, 2010. The disclosures of all of the above-listed prior-filed applications are hereby incorporated by reference herein in their entirety.

TECHNICAL FIELD

The present invention relates to a method and an apparatus for producing a stretchable sheet.

BACKGROUND ART

In a disposable diaper, which is an example of a sanitary article, a stretchable sheet may be used as a fastening member (for example, portions of a front body piece or a rear body piece around a waist) that is fastened around the torso of a wearer. This stretchable sheet is produced by, for example, performing a drawing process on a raw sheet including a nonwoven fabric and the like. A method called "gear drawing" is known as an example of the drawing process (e.g., see PTL 1).

CITATION LIST

Patent Literature

[PTL 1] JP-A-2009-228145

SUMMARY OF INVENTION

Technical Problem

This "gear drawing" is a method in which a raw sheet is drawn by a pair of upper and lower gear rolls having teeth formed on outer circumferential faces thereof at a predetermined arrangement pitch Pt in a circumferential direction. More specifically, the raw sheet is passed through a gap between the pair of rotating upper and lower gear rolls, during which the raw sheet is deformed into a shape bent at three points by the teeth of the upper and lower gear rolls that mesh with one another so as to draw the raw sheet in the direction of rotation of the gear rolls. After such drawing, stretchability is developed in the raw sheet, thereby becoming a stretchable sheet.

In general, an emboss process is performed on the raw sheet. In other words, substantially an entire surface of the raw sheet is provided with an embossed section that is formed in a recessed manner with a predetermined pattern such as a staggered pattern and a lattice pattern to prevent constituent fibers from falling out of the raw sheet.

However, in performing gear drawing on a raw sheet having such embossed sections, a magnitude relationship between an arrangement pitch Pt of teeth of a gear roll and formation pitch Pe in a drawing direction of the embossed sections may produce drawing irregularity and thus there is a possibility of producing a stretchable sheet with drawing irregularity. In other words, the raw sheet may locally include a section that cannot be effectively drawn by the teeth of the gear roll due to the embossed sections, and thus there is a possibility that an uneven stretchable sheet having locally-varying stretchabilities is produced.

The applicant has carried out intense research and found that, concerning this point, an irregularity in stretchability can be suppressed if the relationship in Equation 1 below is satisfied:

$$Pe<Pt<2\times Pe \quad \text{(Eq. 1)}$$

The present invention has been devised in view of above known drawbacks, and it is an object to provide a method and apparatus for producing a stretchable sheet that can evenly develop stretchability in a raw sheet having recessed sections such as embossed sections.

Solution to Problem

In order to achieve the above-described advantages, a principal aspect of the invention is a method of producing a stretchable sheet, the method including:
preparing a pair of gear rolls each having a plurality of teeth arranged on a circumference thereof, the gear rolls being rotatable about respective axes of rotation with the teeth meshing each other; and
drawing a raw sheet in a drawing direction using the teeth by passing the raw sheet through a gap between the pair of gear rolls, the raw sheet containing a plurality of types of fibers, the drawing direction being one of a direction of rotation of the gear roll and a direction parallel to the axes of rotation,
the raw sheet having a plurality of recessed sections formed by pressing, the recessed sections being formed collinearly at least along the drawing direction at a predetermined formation pitch in the drawing direction,
with respect to each gear roll of the pair of gear rolls, an arrangement pitch of the teeth in the drawing direction is greater than the formation pitch and smaller than twice as long as the formation pitch.

Further, another aspect of the invention is an apparatus for producing a stretchable sheet, the apparatus including:
a pair of gear rolls each having a plurality of teeth arranged on a circumference thereof, the gear rolls being rotatable about respective axes of rotation with the teeth meshing each other,
the stretchable sheet being produced by drawing a raw sheet in a drawing direction using the teeth bypassing the raw sheet through the gap between the pair of gear rolls, the raw sheet containing a plurality of types of fibers, the drawing direction being one of a direction of rotation of the gear roll and a direction parallel to the axes of rotation,
the raw sheet having a plurality of recessed sections formed by pressing, the recessed sections being formed collinearly at least along the drawing direction at a predetermined formation pitch in the drawing direction,
with respect to each gear roll of the pair of gear rolls, an arrangement pitch of the teeth in the drawing direction is greater than the formation pitch and smaller than twice as long as the formation pitch.

Features of the invention other than the above will become clear by the description of the present specification and the accompanying drawings.

Advantageous Effects of Invention

According to the present invention, when drawing a sheet by passing it through the gap between a rotating pair of gear rolls, any possible damage of the sheet can be reduced.

BRIEF DESCRIPTION OF DRAWINGS

FIGS. 8A and 8B are plan views of a second example of the arrangement pattern of the embossed sections 11.

MODE FOR CARRYING OUT THE INVENTION

Figure 1:
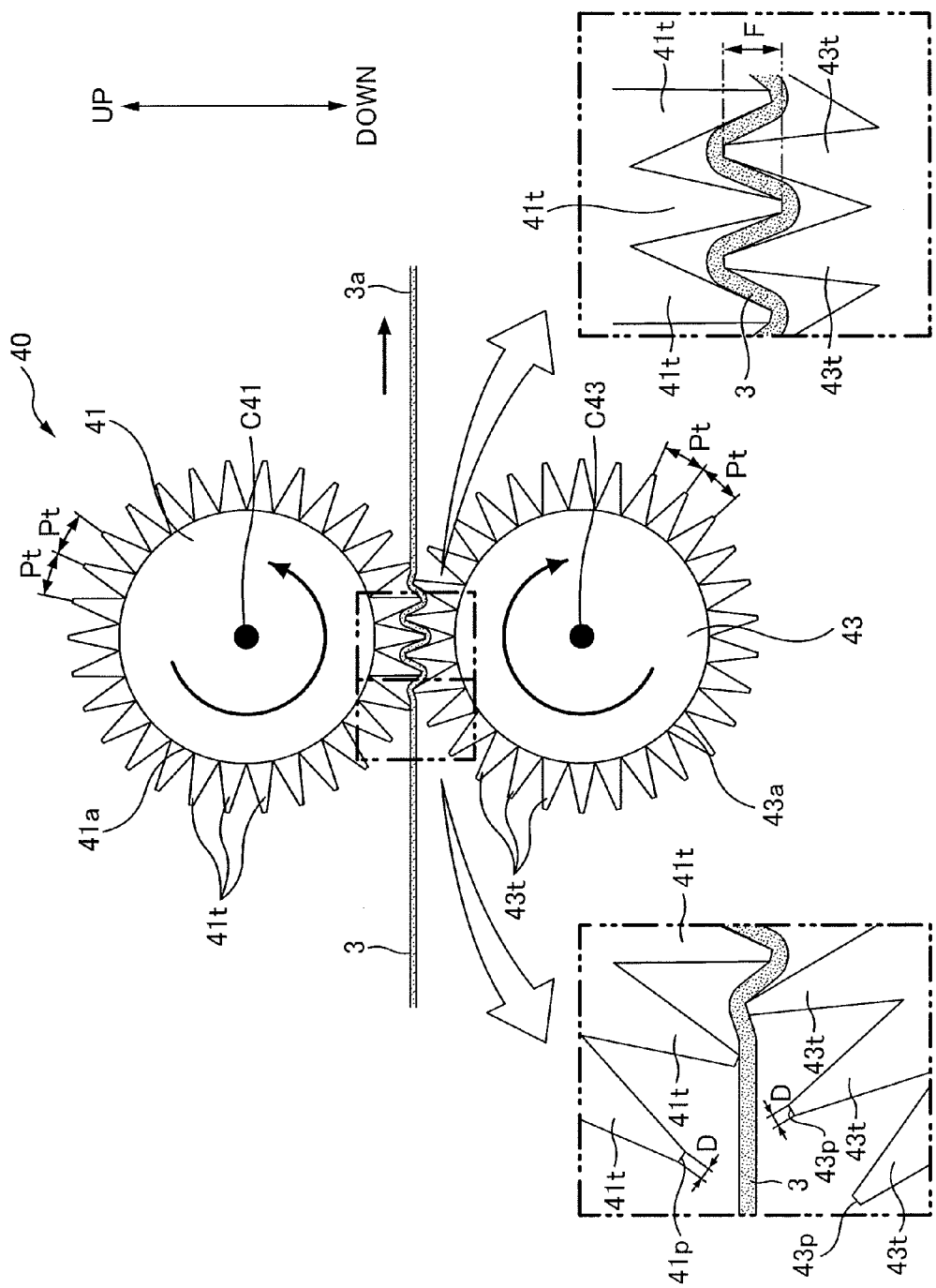
FIG. 1 is an explanatory diagram of a gear drawing apparatus 40 of a first embodiment with a partially enlarged view thereof.

At least the following matters will be made clear by the description of the present specification with reference to the accompanying drawings.

According to an aspect of the present invention, a method of producing a stretchable sheet includes:

preparing a pair of gear rolls each having a plurality of teeth arranged on a circumference thereof, the gear rolls being rotatable about respective axes of rotation with the teeth meshing each other; and drawing a raw sheet in a drawing direction using the teeth by passing the raw sheet through a gap between the pair of gear rolls, the raw sheet containing a plurality of types of fibers, the drawing direction being one of a direction of rotation of the gear roll and a direction parallel to the axes of rotation, the raw sheet having a plurality of recessed sections formed by pressing, the recessed sections being formed collinearly at least along the drawing direction at a predetermined formation pitch in the drawing direction, with respect to each gear roll of the pair of gear rolls, an arrangement pitch of the teeth in the drawing direction is greater than the formation pitch and smaller than twice as long as the formation pitch.

With such a method for producing a stretchable sheet, the above-mentioned Equation 1 is satisfied for the plurality of recessed sections located collinearly at least along a drawing direction. Therefore, at least those recessed sections are less likely to contribute to an irregularity in stretchability of the stretchable sheet. Therefore, the stretchability of the stretchable sheet can be made even.

According to another aspect of the present invention, it is preferable that, in the method for producing a stretchable sheet, the raw sheet includes a plurality of rows of recessed sections, each row including a plurality of the recessed sections arranged collinearly along the drawing direction, the rows being arranged side-by-side in a direction orthogonal to the drawing direction;

in the respective rows of recessed sections, the recessed sections are formed at respective predetermined formation pitches along the drawing direction; and with respect to each one of the rows of recessed sections in the raw sheet, the arrangement pitch of the teeth in the drawing direction is greater than the formation pitch and smaller than twice as long as the formation pitch.

With such a method for producing a stretchable sheet, the above-mentioned Equation 1 is satisfied for each of the rows of recessed sections formed in the raw sheet. Therefore, the stretchability of the stretchable sheet can be made more even.

According to another aspect of the present invention, it is more preferable that, in the method of producing a stretchable sheet, the plurality of rows of recessed sections includes a row of recessed sections whose formation pitch value is a first predetermined value and a row of recessed sections whose formation pitch value is a second predetermined value;

the first predetermined value and the second predetermined value are different from each other;

an arrangement pitch of the teeth in the drawing direction is greater than the first predetermined value and smaller than twice as long as the first predetermined value; and an arrangement pitch of the teeth in the drawing direction is greater than the second predetermined value and smaller than twice as long as the second predetermined value.

With such a method for producing a stretchable sheet, the rows of recessed sections of different formation pitches can be provided in a mixed manner on the raw sheet while achieving evenness in the stretchability. Therefore, a wider variation of arrangement patterns of the recessed sections can be provided.

According to another aspect of the present invention, it is preferable that, in the method of producing a stretchable sheet, fibers constituting the raw sheet are welded with each other at the recessed section; and an arrangement pattern of the plurality of recessed sections in the raw sheet is a staggered arrangement.

With such a method of producing a stretchable sheet, since the raw sheet is welded at each of the recessed sections arranged in a staggered manner, an improved integrity of the stretchable sheet can be achieved.

According to another aspect of the present invention, it is preferable that, in the method of producing a stretchable sheet, the plurality of recessed sections of the raw sheet are also arranged collinearly and form a row of recessed sections in a direction orthogonal to the drawing direction, a plurality of the rows of recessed sections being arranged side-by-side at a second pitch in the drawing direction; and an arrangement pitch of the teeth in the drawing direction is greater than the second pitch and smaller than twice as long as the second pitch.

With such a method for producing a stretchable sheet, the stretchability of the stretchable sheet can made more even.

According to another aspect of the present invention, an apparatus that produces a stretchable sheet includes:

a pair of gear rolls each having a plurality of teeth arranged on a circumference thereof, the gear rolls being rotatable about respective axes of rotation with the teeth meshing each other, the stretchable sheet being produced by drawing a raw sheet in a drawing direction using the teeth bypassing the raw sheet through a gap between the pair of gear rolls, the raw sheet containing a plurality of types of fibers, the drawing direction being one of a direction of rotation of the gear roll and a direction parallel to the axes of rotation, the raw sheet having a plurality of recessed sections formed by pressing, the recessed sections being formed collinearly at least along the drawing direction at a predetermined formation pitch in the drawing direction, with respect to each gear roll of the pair of gear rolls, an arrangement pitch of the teeth in the drawing direction is greater than the formation pitch and smaller than twice as long as the formation pitch.

With such an apparatus which produces a stretchable sheet, the above-mentioned Equation 1 is satisfied for the plurality of recessed sections located collinearly at least along a drawing direction. Therefore, at least those recessed sections are less likely to contribute to an irregularity in stretchability of the stretchable sheet. Therefore, the stretchability of the stretchable sheet can be made even.

First Embodiment

<<Gear Drawing>>

FIG. 1 is an explanatory diagram of gear drawing. Gear drawing is performed using a gear drawing apparatus 40. The gear drawing apparatus 40 includes a pair of upper and lower gear rolls 41, 43, each having substantially the same shape as each another and rotating about one of the axes of rotation C41, C43. Specifically, on an outer circumferential portion 41*a*, 43*a* of each gear roll 41, 43, teeth 41*t*, 43*t* (teeth having a tooth shape that is substantially the same as those of a so-called "spur gear") are provided in a substantially corrugated shape at an equal arrangement pitch Pt along a direction of rotation thereof.

While these gear rolls 41, 43 are driven and are rotating at a constant peripheral speed S, a sheet 3 is passed through a gap between the gear rolls. The sheet 3 is thus deformed by being bent at three points by the teeth 41*t* of the upper gear roll 41 and the teeth 43*t* of the lower gear roll 43 that mate with each another (see an enlarged view on the right in FIG. 1), and is drawn in the direction of rotation. After being drawn in this manner, stretchability is developed in the nonwoven fabric 3, thereby becoming a stretchable sheet 3*a*.

Hereinafter, a transport direction in which the raw sheet 3 is passed through will also be referred to as an "MD-direction", and, among directions orthogonal to the MD-direction, a direction parallel to a width direction of the raw sheet 3 will also be referred to as a "CD-direction". It is to be noted that the axes of rotation C41, C43 of the upper and lower gear rolls 41, 43 are oriented in the CD-direction.

The raw sheet 3 used as a material in such gear drawing is, for example, a nonwoven fabric, and specifically, a nonwoven fabric 3 that is produced by blending an extensible fiber and a stretchable fiber in a predetermined mixing ratio by melt spinning or the like. Here, the stretchable fiber is a fiber that can extend elastically and the extensible fiber is a fiber that can extend in a substantially non-elastic manner. In other words, the extensible fiber may be defined as a fiber that undergoes plastic deformation with an elongation smaller than the elongation at an elastic limit of the stretchable fiber.

An example of the extensible fiber is a thermoplastic polyolefin fiber, and an example of the stretchable fiber is a thermoplastic elastomeric fiber. Examples of the thermoplastic polyolefin fiber include single fibers, such as a polypropylene fiber and a polyester fiber, and a conjugate fiber with a sheath core structure consisting of polypropylene or polyester, and examples of the thermoplastic elastomeric fiber include a polyurethane fiber.

The methods for producing the nonwoven fabric 3 include, for example, a spunbonding method or a chemical-bonding method. Basis weight and fiber diameter of the nonwoven fabric 3 are suitably selected from, for example, ranges of 20 to 50 (g/m$^2$) and 10 to 30 ($\mu$m), respectively. Furthermore, the mixing ratio of the extensible fiber and the stretchable fiber is suitably selected from a range of 20 to 80%.

An arrangement pitch Pt of the teeth 41 (the pitch at a top section 41*p* (43*p*) of the teeth 41*t* (43*t*)) of the gear roll 41 (43) is selected from a range of 1 to 6 (mm), and preferably from a range of 2 to 3 (mm). A diameter $\phi$ of the gear roll 41 (43) (the diameter at the top portion 41*p* (43*p*)) is selected from a range of 120 to 600 (mm). The peripheral speed S of the gear roll 41 (43) (the speed at the top section 43*p*) is selected from, for example, a range of 50 to 300 (m/min). The top section 41*p* (43*p*) of the tooth 41*t* (43*t*) is formed as a flat surface along the direction of rotation, and a length D in the rotation of direction of the flat surface is selected from a range of 0.1 to 0.4 mm. A total length (total width) of the teeth 41*t* (43*t*) in the CD direction is greater than a total length (total width) of the raw sheet 3 in the CD direction, and thus, during a drawing process, the top section 41*p* (43*p*) of the teeth 41*t* (43*t*) comes into contact with the raw sheet 3 for substantially the entire width of the raw sheet 3.

A maximum mating depth F between the upper gear roll 41 and the lower gear roll 43 is determined based on a drawing distortion $\epsilon_{all}$ to be applied to the nonwoven fabric 3 during drawing (see Equation 3 described later) and thus, the arrangement pitch Pt, is selected from the above-described range in such a manner that a drawing distortion $\epsilon_{all}$ selected from a range of 0.6 to 3.0 is achieved.

Now, the drawing distortion $\epsilon_{all}$ described above can be defined in a similar manner to the concept of an ordinary distortion and can be defined by Equation 2 below, using a total length Lb in the drawing direction during the drawing process and a total length La in the drawing direction before the drawing process:

$$\epsilon_{all}(Lb-La)/La \qquad \text{(Eq. 2)}$$

In the case of gear drawing, the drawing distortion $\epsilon_{all}$ expressed on the basis of the geometrical relationship regarding the mating between the teeth 41*t* and 43*t*, or, in other words, as a function of the maximum mating depth F between the teeth 41*t* and 43*t* and the arrangement pitch Pt of the teeth 41*t* (43*t*). Specifically, since the original length of Pt of the nonwoven fabric 3 near a mating start point is deformed and drawn, in a maximum mating point during drawing shown in the enlarged view on the right side of FIG. 1B by being bent at three points by the teeth 41*t* and 43*t* that mate with each other with a maximum mating depth F, the drawing distortion $\epsilon_{all}$ can be substantially expressed as Equation 3 below:

$$\epsilon_{all} 2 \times (\sqrt{(F^2 + (Pt/2)^2)} - (Pt/2))/Pt \qquad \text{(Eq. 3)}$$

Figure 2A:
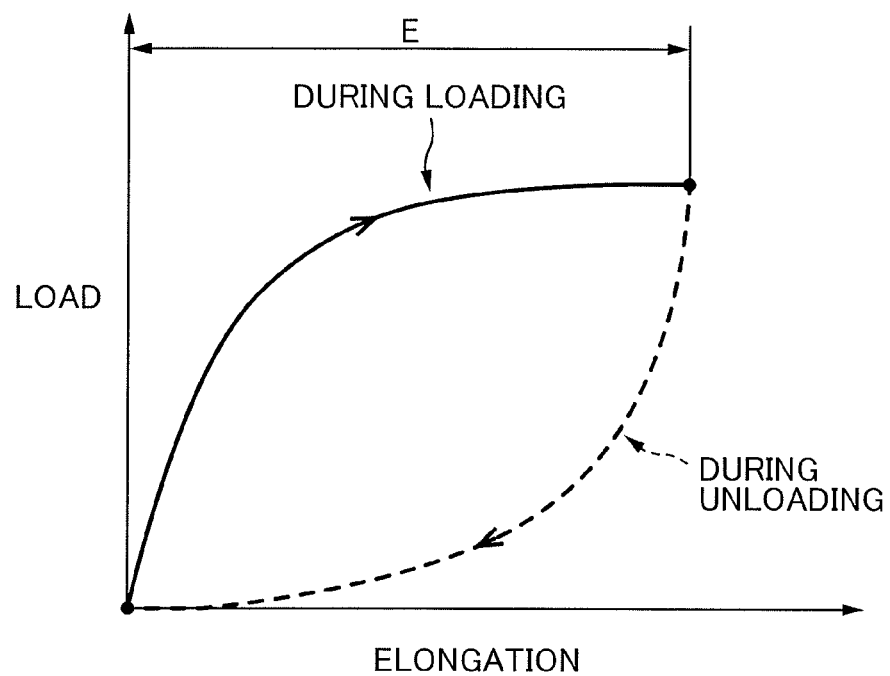
FIGS. 2A and 2B are explanatory diagrams showing a mechanism in which stretchability is developed in a nonwoven fabric 3 due to a drawing process, and showing load-elongation curves for the nonwoven fabric 3.
Figure 2B:
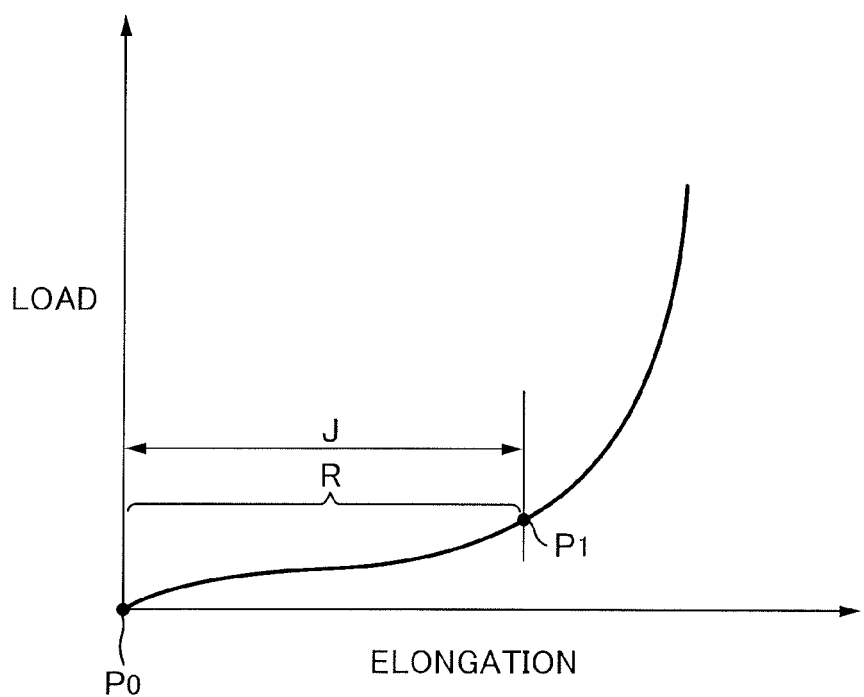

FIGS. 2A and 2B are explanatory diagrams of a mechanism in which stretchability is developed in the nonwoven fabric 3 by a drawing process. Each diagram shows a load-elongation curve of the nonwoven fabric 3.

When a tension (hereinafter also referred to as a "load") is applied to the nonwoven fabric 3 within the elastic limit of the stretchable fiber in order to perform the drawing process on an undrawn nonwoven fabric 3, the load-elongation curve shown in FIG. 2A is obtained during such drawing process. That is to say, the obtained load-elongation curve includes a hysteresis in which a load under the same elongation is lower when the tension is being unloaded than when the tension is being loaded.

And, in the case where the tension is applied again after the drawing process, the load-elongation curve shown in FIG. 2B will be plotted. In detail, it stretches at a significantly low elastic modulus from the origin P0 to an inflection point P1 in FIG. 2B. However, once it exceeds the inflection point P1, the load rapidly increases in a substantially quadric curve form. And normally, with an appearance of this low elastic modulus range R, the stretchability is considered to have been developed in the nonwoven fabric 3 by the drawing process. Further, an elongation amount J from the origin P0 in an unloaded state to the inflection point P1 is defined as a "developed stretch amount J".

Incidentally, the reason why the nonwoven fabric 3 stretches at a significantly low elastic modulus from the origin P0 to the inflection point P1 after the drawing process can be explained, as below.

Figure 3A:
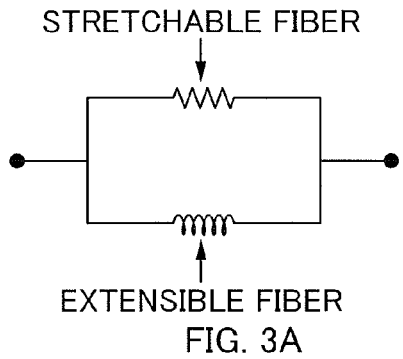
FIG. 3A is a schematic view showing the state of fibers before the drawing process.
Figure 3B:
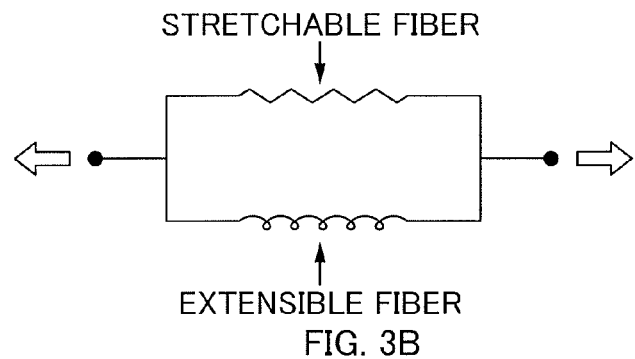
FIG. 3B is a schematic view showing the state of fibers during the drawing process.
Figure 3C:
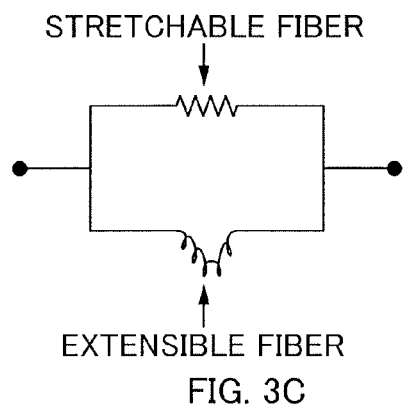
FIG. 3C is a schematic view showing the state of fibers after the drawing process.

FIG. 3A is a schematic view showing the state of fibers before the drawing process (i.e., an undrawn state). FIG. 3B is a schematic view showing the state of fibers during the drawing process (i.e., during loading). FIG. 3C is a schematic view showing the state of fibers after the drawing process (i.e., after unloading). Note that, generally, a minimum unit structure constituting the nonwoven fabric 3 can be modeled as a parallel connection of the stretchable fiber and the extensible fiber, as shown in FIG. 3A.

In the case where the undrawn nonwoven fabric 3 shown in FIG. 3A is drawn, as can be seen in FIG. 3B, the stretchable fiber undergoes elastic deformation, whereas the extensible fiber whose elongation at the elastic limit is smaller than that of the stretchable fiber, undergoes plastic deformation at a comparatively early stage and is elongated by plastic deformation. Accordingly, when the tension is released from this state, as shown in FIG. 3C, the stretchable fiber will simply be free of elastic elongation; in other words, a total length thereof returns to substantially the same as the length prior to applying the tension. However, the extensible fiber will have a total length that has been elongated by the amount of plastic elongation and the extensible fiber becomes slack.

Figure 3D:
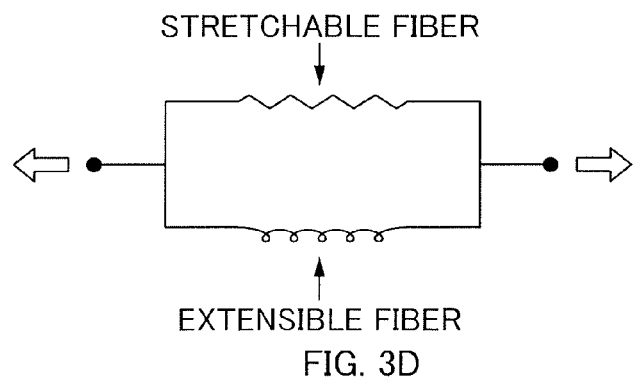
FIG. 3D is a schematic view showing the state of fibers when the nonwoven fabric 3 is drawn again after the drawing process.

And, when the tension is applied again to the nonwoven fabric 3 that has undergone the drawing process, the nonwoven fabric 3 resists the above tension only by the elastic deformation of the stretchable fiber until the slack portion of the extensible fiber is fully extended and the entire length thereof is tensed. Therefore, as shown in FIG. 2B, the nonwoven fabric 3 is extended at a significantly low elastic modulus. However, as shown in FIG. 3D, from the point at which there is no more above-mentioned slack in the extensible fiber and the extensible fiber is stretched over the entire length thereof, the elastic-plastic deformation of the extensible fiber also starts to resist the tension. Accordingly, the tension required to extend the nonwoven fabric 3 rapidly increases from this point. That is, the point at which the slack in the extensible fiber disappears is the inflection point P1 in FIG. 2B, and based on the descriptions given so far, as shown in FIG. 2B, the load-elongation curve after the drawing process indicates that the nonwoven fabric 3 is stretched at an extremely low elastic modulus until the inflection point P1, and the load rapidly increases after exceeding the inflection point P1. Incidentally, it goes without saying that when the tension is released within the range R from the origin P0 to the inflection point P1, namely, within the range R of the "developed stretch amount J", the load-elongation curve substantially tracks back along the load-elongation curve for loading shown in FIG. 2B, and returns to the origin P0.

<<Effect of Embossed Section 11 on Development of Stretchability in Raw Sheet>>

In general, the raw sheet 3 is provided with embossed sections 11, 11, . . . , which are examples of recessed sections, formed in a recessed manner in a predetermined arrangement pattern by an emboss process, which is an example of a pressing process. In an example shown in the plan view of FIG. 4, these are formed in a lattice manner along both the MD-direction and the CD-direction. At each of the embossed sections 11, 11, . . . , the fibers at such sections are welded with each other and thus the raw sheet 3 is provided in an integrated manner.

Figure 5A:
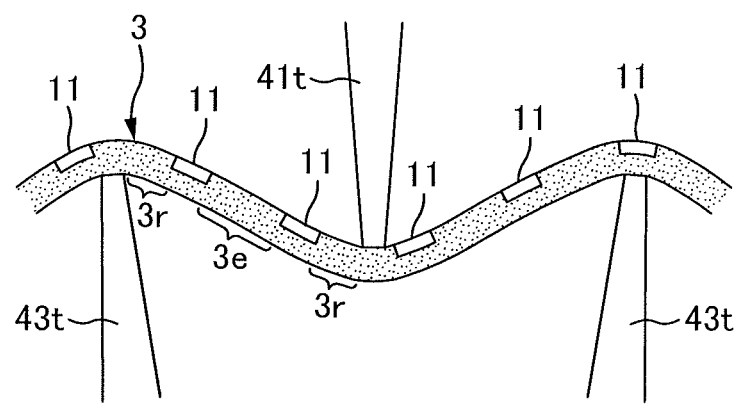
FIG. 5A is an explanatory diagram for a case where the development of stretchability is locally and significantly inhibited and FIG. 5B is an explanatory diagram for a case where it is not inhibited so much.
Figure 5B:
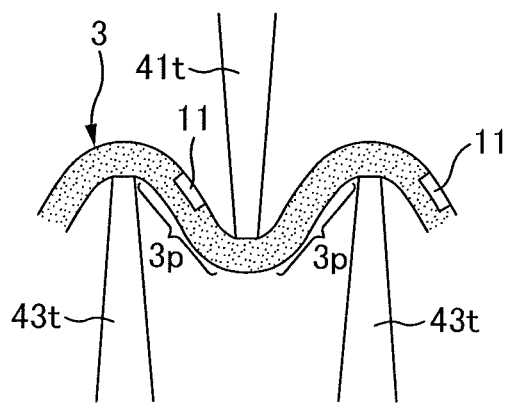

However, such embossed sections 11 may locally inhibit the development of stretchability in the raw sheet 3. FIGS. 5A and 5B are explanatory views thereof. FIG. 5A shows a case in which the development of stretchability is locally and largely inhibited and FIG. 5B shows a case where it is not so inhibited.

For example, as in the latter case of FIG. 5B, in a case where there is only a single embossed section 11 or there is no embossed section 11 between the tooth 41t of the upper gear roll 41 (hereinafter also referred to as an upper tooth 41t) and the tooth 43t of the lower gear roll 43 (hereinafter also referred to as a lower tooth 43t), a section 3p of the raw sheet 3 that is located between the upper tooth 41t and the lower tooth 43t will be drawn to a target drawing amount rapidly and without a significant problem. Therefore, a stretchability of generally the target level will be achieved.

On the other hand, as shown in FIG. 5A, in a case where two embosses 11 and 11 exist between the upper tooth 41t and the lower tooth 43t, it will be difficult for a tension related to the drawing to be transmitted from the upper tooth 41 and the lower tooth 43t to a section 3e (hereinafter also referred to as an inter-emboss section) between the embossed section 11 and the embossed section 11, and thus the drawing will not be achieved to the target drawing amount, resulting in an insufficient drawing section. Accordingly, the section 3e will not develop the stretchability of the target level. That is to say, the stretchability will be lower than that of a section 3r which is a surrounding section and which has been drawn to a target drawing amount. As a result, there will be a considerable stretch irregularity in the stretchable sheet 3a.

The reason why a tension is difficult to be transmitted to the inter-emboss section 3e is as follows. Normally, the embossed section 11 has a low strength since it is a section with altered quality due to pressing, welding and the like between the fibers and the embossed section 11 is likely to be subjected to a more concentrated stress than surrounding sections since it can be regarded as a kind of inclusion and thus it is likely to be torn. Therefore, before a tension from the upper tooth 41t and the lower tooth 43t related to drawing is transmitted to the inter-emboss section 3e, transmission of the tension will be inhibited due to a tear and the like at the embossed section 11 and, as a result, it will be difficult for the inter-emboss section 3e to be drawn.

Figure 4:
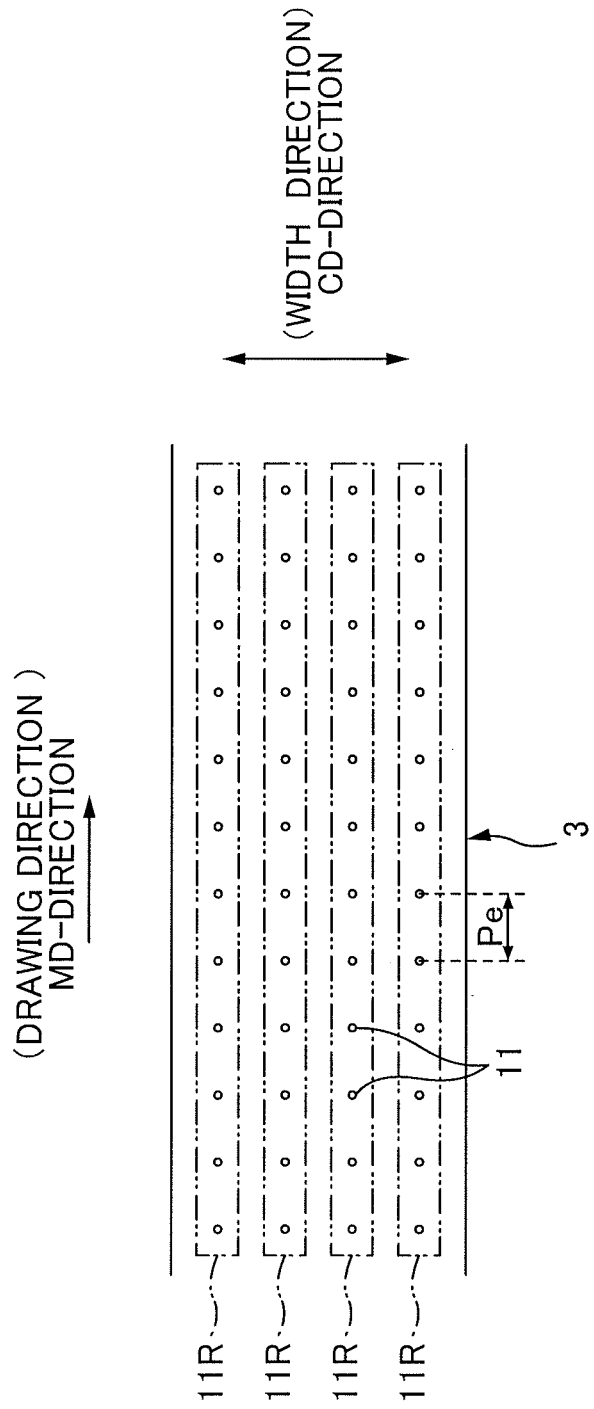
FIG. 4 is a plan view of a raw sheet 3.

Here, it is considered that the above-mentioned tension related to drawing acts linearly in the drawing direction. Therefore, in order to prevent an occurrence of an insufficiently drawn section as described above, it can be considered that, as shown in FIG. 4, when particularly focusing on the embossed sections 11, 11, . . . which are provided collinearly along the drawing direction, the number of embossed sections 11 provided between the upper tooth 41t and the lower tooth 43t should always be one or less than one for every row of embossed sections 11R each including embossed sections 11, 11, . . . which have been particularly focused on. This condition can be expressed by Equation 4 below:

$$Pt \leq 2 \times Pe \quad \text{(Eq. 4)}$$

where Pe is a formation pitch of the embossed sections 11, 11, . . . provided collinearly along the drawing direction, and Pt is an arrangement pitch of the teeth 41t (43t) of the gear roll 41 (43).

That is to say, the arrangement pitch Pt of the teeth 41t (43t) may be less than or equal to a multiple of two of the formation pitch Pe of the embossed sections 11, 11, . . . provided collinearly along the drawing direction.

Figure 6A:
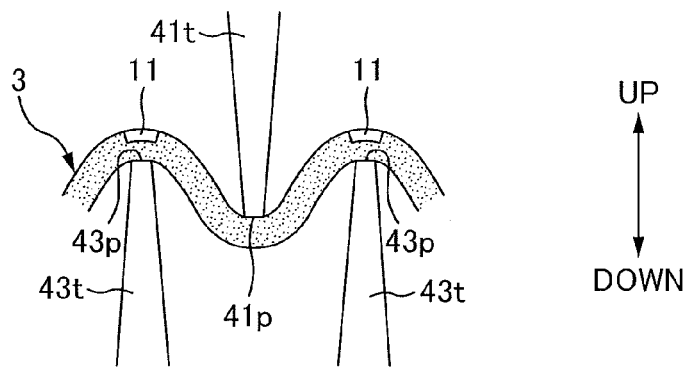
FIGS. 6A to 6C are conceptual views for explaining that irregularity in stretchability may become great when Pt=Pe and Pt=2×Pe.
Figure 6B:
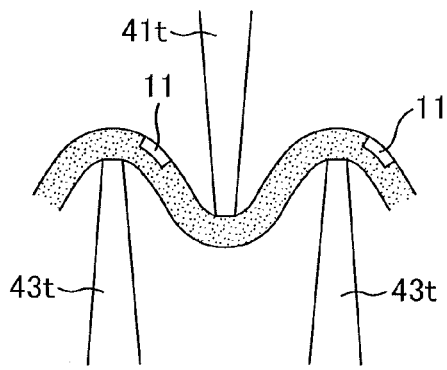

However, even when the relationship expressed by Equation 4 mentioned above is satisfied, there may be a case where there is a considerable stretch irregularity. This occurs when Pe=Pt. FIGS. 6A and 6B are diagrams describing such a case.

For example, as shown in FIG. 6A, in the case of Pe=Pt, the formation pitch Pe of the embossed sections 11 and the arrangement pitch Pt of the lower teeth 41t naturally match. Therefore, depending on the case, as shown in FIG. 6A, the lower teeth 43t and the lower teeth 43t which are adjacent to each other come into contact with corresponding emboss sections 11, 11, respectively. This is the positional relationship in which the highest stretchability is developed. This will be described in detail below.

The embossed section 11 has been altered in its quality and thus it is a section that is not likely to contribute to the development of stretchability. On the other hand, with respect to the gear roll 43 (41), since the raw sheet 3 is drawn between the tooth 43t and the tooth 41t, the peak section 43p (41p) at the tip of the tooth 43t (41t) is also a portion that is difficult in contributing to the development of stretchability. Therefore, the positional relationship in which the sections that are difficult for contributing to the development of stretchability, i.e., the embossed section 11 and the peak section 43p (41p) of the tooth 43t (41t), are in contact with each other is a positional relationship in which the stretchability is developed the most.

However, since the raw sheet 3 stretches in response to the tension, it is difficult to maintain this positional relationship all the time during the drawing process. That is to say, in practice, it is considered that it will repeatedly come to such a positional relationship (FIG. 6A) and become offset from such a positional relationship in the MD-direction (FIG. 6B) in response to rotation of the gear rolls 41, 43. As a result, it is considered that the sections in which the stretchability has been developed the most and the remaining sections repeatedly appear in the MD-direction in the produced stretchable sheet 3a and thus there may be a considerable irregularity in stretchability. One way of preventing this is to avoid the above-mentioned positional relationship (FIG. 6A) where the stretchability is developed the most.

Accordingly, a situation where Pe=Pt should be excluded from the condition of the above-mentioned Equation 4 and by taking this into consideration, Equation 5 described below is a condition in which an evenness in the stretchability of the stretchable sheet 3a can be improved.

$$Pe < Pt \leq 2 \times Pe \quad \text{(Eq. 5)}$$

Figure 6C:
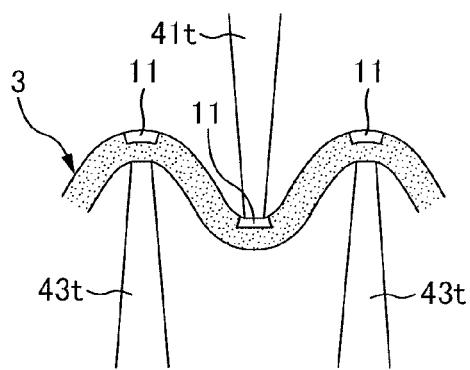

It is to be noted that a situation where Pt=2×Pe should also be excluded from the condition expressed by Equation 5. This is because Pt=2×Pe will also give a positional relationship similar to the case of Pt=Pe described above (see FIG. 6C). Therefore, further taking this into consideration, a condition that can improve evenness in stretchability will be as expressed in Equation 6 below:

$$Pe < Pt < 2 \times Pe \quad \text{(Eq. 6)}$$

<<Illustrative Arrangement Pattern of Embossed Section 11>>

Figure 7:
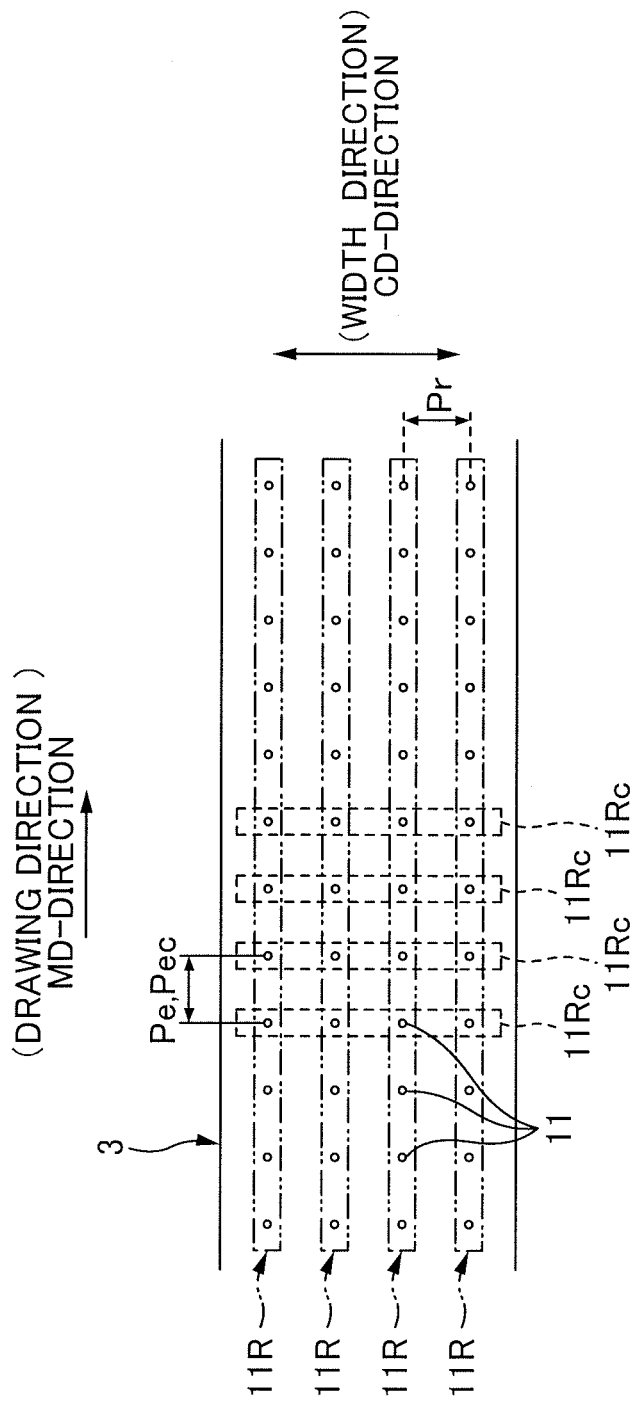
FIG. 7 is a plan view of a first example of an arrangement pattern of embossed sections 11.
Figure 9:
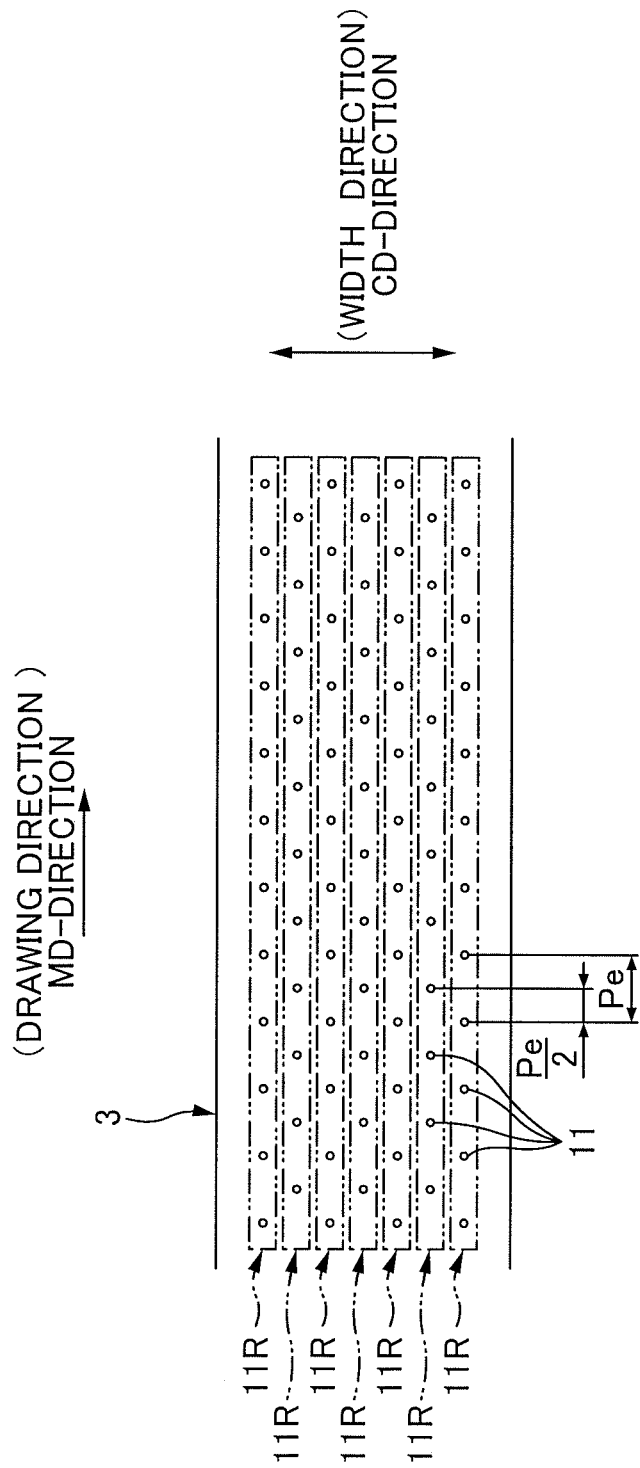
FIG. 9 is a plan view of a third example of an arrangement pattern of embossed sections 11.

The above-mentioned Equation 6 will be described with reference to an illustrative arrangement pattern of embossed section 11. FIGS. 7 to 9 show plan views of the raw sheet 3 provided as illustrative views.

FIG. 7 is an illustrative view of a first example of the arrangement pattern of the embossed sections 11. This arrangement pattern is a so-called lattice pattern. That is to say, the raw sheet 3 has rows of embossed sections 11R (corresponds to rows of recessed sections) in which the embossed sections 11, 11, . . . are arranged at a predetermined pitch Pe in the MD-direction and such rows of recessed sections 11R are provided in such a manner that a plurality of rows are arranged in the CD-direction and positions of the embossed sections 11 in the MD-direction are aligned with each other in every row of embossed sections 11R, 11R.

In this example, the formation pitch Pe of the embossed sections 11 in the MD-direction which corresponds to the drawing direction is provided in such a manner that it satisfies the above-mentioned Equation 6 with respect to the arrangement pitch Pt of the teeth 41t (43t). Therefore, in such a case, all of the rows of embossed sections 11R, 11R, . . . will satisfy the relationship of Equation 6 and thus the inhibition of stretchability can be almost entirely suppressed.

In the case of such a lattice pattern, the relationship of Equation 6 can be described as follows. First, the above-mentioned embossed sections 11, 11, . . . are also aligned collinearly in the CD-direction, which is orthogonal to the drawing direction, to form a row of embossed sections 11Rc, and a plurality of the rows of embossed sections 11Rc are provided at a second pitch Pec in the MD-direction, which is the drawing direction. The arrangement pitch Pt of the teeth 41t (43t) is greater than the above-mentioned second pitch Pec and smaller than twice as long as the above-mentioned second pitch Pec.

FIGS. 8A and 8B are illustrative views of a second example of the arrangement pattern. The difference from the first example resides in that a row of embossed sections 12R having a different formation pitch Pe2 is additionally provided along the MD-direction between the rows of embossed sections 11R and 11R that form the above-mentioned lattice pattern.

That is to say, in a case where the row of embossed sections 11R forming the lattice pattern is taken as a first row of emboss patterns 11R and the additionally provided row of embossed sections 11R is taken as the second row of embossed sections 12R, in the example shown in FIG. 8A, the formation pitch Pe2 (corresponding to a second predetermined value) of embossed sections 12, 12, ... belonging to the second row of embossed sections 12R is provided as a value different from the formation pitch Pe (corresponding to a first predetermined value) of the embossed sections 11, 11, ... belonging to the first row of embossed sections 11R.

Here, it is preferable that 11R and 12R both satisfy the above-mentioned Equation 6. Then, inhibition of evenness of stretchability can be almost entirely suppressed.

However, in order to find a Pt that satisfies Equation 6 for both of the rows of embossed sections 11R and 12R, the formation pitch Pe related to the first row of embossed sections 11R and the formation pitch Pe2 related to the second row of embossed sections 12R should satisfy Equation 7 below.

$$0.5 \times Pe < Pe2 < 2 \times Pe \qquad \text{(Eq. 7)}$$

In the case of the example shown in FIG. 8A, since Pe=1.5×Pe, Equation 7 is satisfied. Therefore, a Pt can be found that satisfies Equation 6 for both of the rows of embossed sections 11R and 12R. However, in the case of the example of FIG. 8B, since Pe2=0.4×Pe, Equation 7 is not satisfied and therefore only one of the rows of embossed sections 11R and 12R can satisfy Equation 6. Therefore, considered from the view point of suppressing the irregularity in stretchability, the example of FIG. 8A is more preferable than the example of FIG. 8B.

However, even in the case of FIG. 8B, since one of the rows, e.g., the first row of embossed sections 11R, can satisfy the relationship of Equation 6, a considerable effect in providing evenness in stretchability can be obtained. In other words, in an extreme case, a considerable effect in providing evenness can be obtained provided that there is at least a single row of embossed sections 11R satisfying Equation 6.

The above-mentioned Equation 7 can be derived based on the following idea. First, with regards to the first row of embossed sections 11R, Equation 6 can be expressed as the following Equation 8:

$$Pe < Pt < 2 \times Pe \qquad \text{(Eq. 8)}$$

With regards to the second row of embossed sections 12R, Equation 6 can be expressed as Equation 9 below:

$$Pe2 < Pt < 2 \times Pe2 \qquad \text{(Eq. 9)}$$

Now, taking Pe2=α×Pe, and substituting this into Equation 9, Equation 9 can be expressed as Equation 10 below:

$$\alpha \times Pe < Pt < 2 \times \alpha \times Pe \qquad \text{(Eq. 10)}$$

Therefore, if a Pt satisfying Equations 8 and 10 exists, it can be said that there is a Pt that satisfies Equation 6 for both the first row of embossed sections 11R and the second row of embossed sections 12R. However, to achieve this, Equation 11 needs to be satisfied based on the magnitude relationship between the left hand side of Equation 8 and the right hand side of Equation 10 and also to satisfy Equation 12 based on the magnitude relationship between the right hand side of Equation 8 and left hand side of Equation 10.

$$Pe < 2 \times \alpha \times Pe \qquad \text{(Eq. 11)}$$

$$\alpha \times Pe < 2 \times Pe \qquad \text{(Eq. 12)}$$

Rewriting these equations, Equation 13 below can be obtained.

$$0.5 < \alpha < 2 \qquad \text{(Eq. 13)}$$

Here, since Pe2=α×Pe, as described above, substitution of α=Pe2/Pe into Equation 13 gives Equation 14 below, and thus the above-mentioned Equation 7 can be derived.

$$0.5 \times Pe < Pe2 < 2 \times Pe \qquad \text{(Eq. 14)}$$

FIG. 9 is an illustrative view of a third example of the arrangement pattern. As can be seen from FIG. 9, the arrangement pattern is a so-called staggered arrangement. That is to say, the raw sheet 3 has rows of embossed sections 11R in which the embossed sections 11, 11, ... are arranged at a predetermined pitch Pe in the MD-direction and such rows of recessed sections 11R are provided in such a manner that a plurality of rows are arranged in the CD-direction. Further, positions of the rows of embossed sections 11R, 11R that are adjacent to each other in the CD-direction are mutually offset by half the formation pitch Pe (=Pe/2) in the MD-direction.

In this example, the formation pitch Pe in the MD-direction of the embossed sections 11, 11, ... of each of the rows of embossed sections 11 is determined to satisfy the relationship of Equation 6. Therefore, also for this staggered arrangement, when focusing only on each of the rows of embossed sections 11R, Equation 6 is satisfied for all the rows of the embossed sections 11R. As a result, inhibition of evenness of stretchability can be effectively suppressed.

Second Embodiment

Figure 10B:
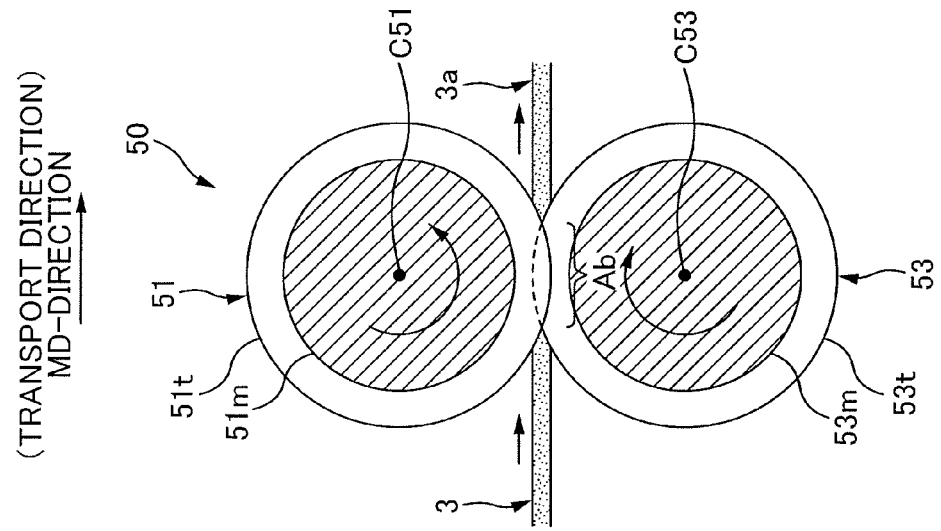
FIG. 10A is a front view of a gear drawing apparatus 50 of a second embodiment and FIG. 10B is a cross sectional diagram taken along B-B in FIG. 10A.
Figure 10A:
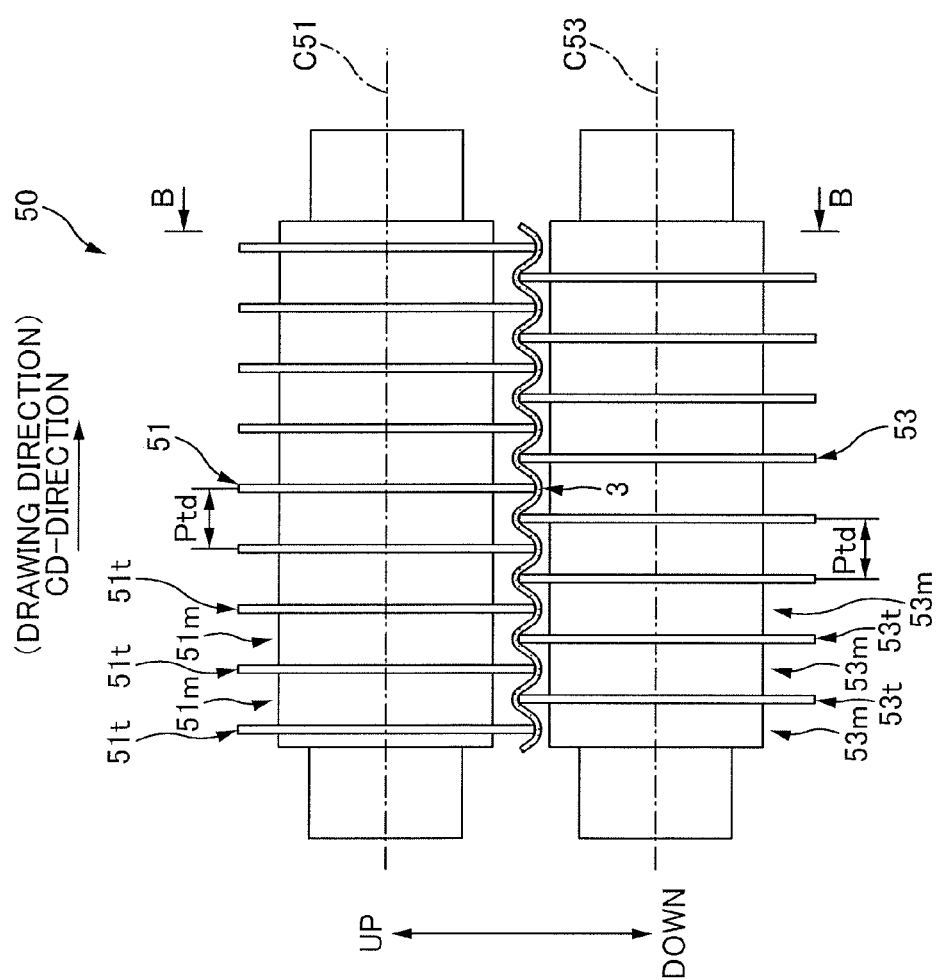

FIGS. 10A and 10B are explanatory views of a gear drawing apparatus 50 of a second embodiment. FIG. 10A is a front view and FIG. 10B is a sectional view taken along B-B in FIG. 10A.

The second embodiment differs from the first embodiment described above in which the raw sheet 3 is drawn in a continuous direction thereof, i.e., the MD-direction, in that the raw sheet 3 is drawn in a width direction thereof, i.e., the CD-direction that corresponds to "a direction parallel to the axes of rotation". Due to this difference, there is also a difference in structure of the teeth 51t, 53t of the gear rolls 51, 53.

Specifically, as shown in FIGS. 10A and 10B, the gear drawing apparatus 50 includes a pair of upper and lower gear rolls 51, 53, each being capable of rotating about respective axes of rotation C51, C53. The upper gear roll 51 includes major diameter sections 51t and minor diameter sections 51m that are alternately arranged along a direction of the axis of rotation C51 and the lower gear roll 53 similarly includes major diameter sections 53t and minor diameter sections 53m that are alternately arranged along a direction of the axis of rotation C53. These gear rolls 51, 53 are arranged one above the other with the major diameter section 51t, 53t of one of the gear rolls being inserted between the minor diameter section 53m, 51m of the other gear roll. Thus, the major diameter section 51t, 53t of each is mated to the other in a tooth-like manner in a region Ab that is a part of the gear rolls 51, 53 in the circumferential direction. Hereinafter, this region Ab will be referred to as a "mating region Ab". (See FIG. 10B.)

Here, the raw sheet 3 is transported towards the mating region Ab and, while passing the mating region Ab, is drawn in the CD-direction by being deformed into a shape bent at three points as shown in FIG. 10A. Then, after being drawn, the stretchability in the CD-direction will develop and thus a stretchable sheet 3a having stretchability in the width direction will be produced.

Therefore, the second embodiment differs from the first embodiment in that the drawing direction is CD-direction, instead of MD-direction.

Figure 11:
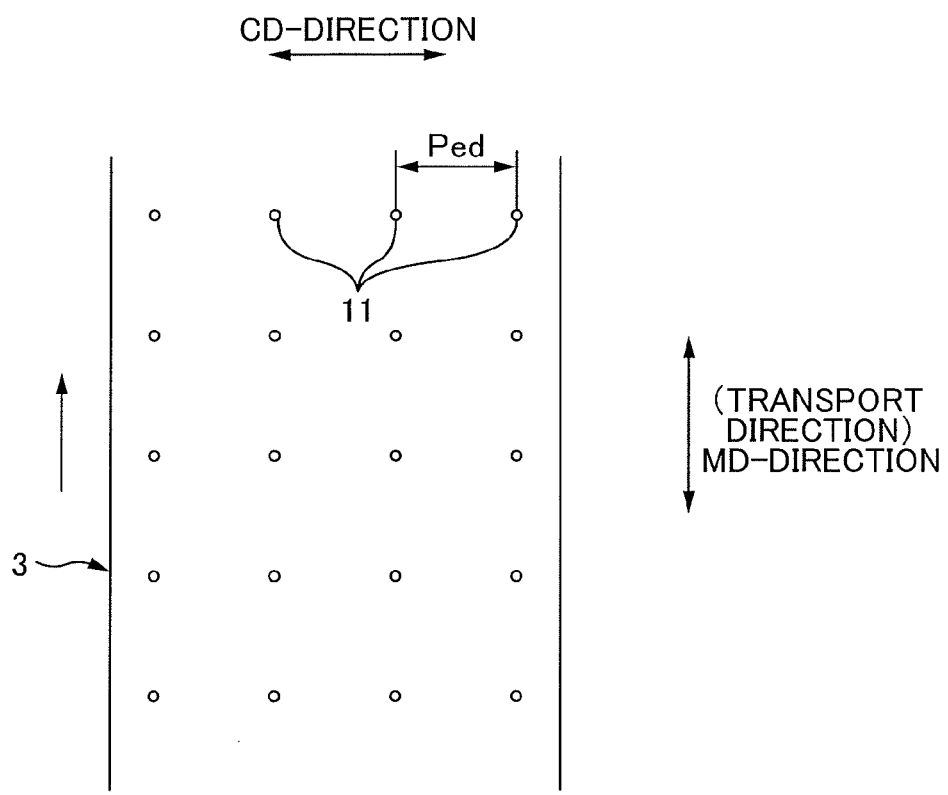
FIG. 11 is a plan view of a raw sheet 3 of the second embodiment.

Based on the above, in the second embodiment, considering that the formation pitch Ped in the CD-direction of the embossed sections 11 of FIG. 11 corresponds to the formation pitch Pe of the above-mentioned first embodiment and that the arrangement pitch Ptd in the CD-direction of the major diameter sections 51*t* (53*t*), corresponding to the teeth in FIG. 10A, corresponds to the arrangement pitch Pt in the above-mentioned first embodiment, the explanation described for the first embodiment can be applied to the second embodiment. Therefore, such explanation will be omitted.

Other Embodiments

Embodiments of the present invention have been described as above, however the present invention is not limited to these embodiments and the following variants are also possible.

In the above embodiment, a nonwoven fabric that includes two types of fibers, i.e., the extensible fiber and the stretchable fiber, has been illustrated as the raw sheet 3 including a plurality of types of fibers. However, the number of types of fibers is by no means limited to two, and may be three or more types.

In the above embodiment, a nonwoven fabric of a type in which the extensible fiber and the stretchable fiber are blended has been illustrated as the raw sheet 3 including a plurality of types of fibers. However, this can be of a type in which layers of the extensible fiber only and layers of the stretchable fiber only are provided in separate layers which are layered in a thickness direction of the nonwoven fabric. The number of layers is not limited to two, and, for example, may be a nonwoven fabric of a three-layer structure in which a layer of stretchable fiber only is sandwiched between upper and lower layers of extensible fiber only.

In the above embodiment, the gear drawing apparatus 40, 50 has been mainly described as an apparatus relating to a production method by gear drawing, but an appropriate auxiliary device may also be provided. For example, a plurality of tension rolls may be respectively disposed in an upstream position of the gear drawing apparatus 40, 50 so as to apply a tension to the raw sheet 3 and thus a preliminary drawing process may be applied before the gear drawing. Further, a heater or the like that heats the gear rolls 41 and tension rolls may also be disposed and a suction conveyor that is capable of reducing transport tension may be used for transporting the stretchable sheet 3*a* after the drawing process.

In the description of the embodiments above, although a detailed explanation has not been made on the shape of an embossed section 11, the shape of the embossed section 11 is a recessed section having a base surface of a predetermined area. The shape of the base surface is, for example, a circular shape such as a perfect circle and a polygon such as a square and a rhombus. Further, the base surface has an area of, for example, 0.2 to 4 mm$^2$. The embossed section 11 of such a configuration is formed by being pressed with a plurality of protruded sections on the circumferential surface of at least one of the rolls while the sheet that is to become the raw sheet 3 is passing through a roll gap between the pair of rotating upper and lower rolls. In order to improve the welding property between the fibers during the pressing, these rolls may be heated.

In the description of the embodiments above, specific numerical values of the formation pitches Pe, Pec, Ped of the embossed section 11 have not been described, but the value of these formation pitches Pe, Pec, Ped are selected from, for example, 1 to 20 mm, so as to satisfy Equation 6. The range of the above-mentioned numerical value is preferably 1 to 10 mm, and more preferably 1 to 3 mm.

Further, the pitch Pr (FIG. 7) between the rows of embossed sections 11R and 11R will be appropriately selected from 1 to 20 mm.

In the above-mentioned embodiment, the embossed section has been illustrated as an example of the recessed section formed by the pressing process. However, it is by no means limited thereto as long as it is a recessed section formed by pressing.

The invention claimed is:
1. An apparatus configured to produce a stretchable sheet, the apparatus comprising:
a forming section configured to form a plurality of recessed sections in a raw sheet by pressing the raw sheet, the plurality of recessed sections being formed collinearly at least along a drawing direction in the drawing direction;
a pair of gear rolls; and
a supply section configured to supply the raw sheet having the plurality of recessed sections to the pair of gear rolls,
wherein
each gear roll of the pair of gear rolls has a plurality of teeth arranged on a circumference thereof, the pair of gear rolls being rotatable about respective axes of rotation with the plurality of teeth meshing with each other,
the plurality of teeth of the pair of gear rolls is configured to draw the raw sheet, on which the plurality of recessed sections has been formed, in the drawing direction by passing the raw sheet through a gap between the pair of gear rolls, the raw sheet containing a plurality of types of fibers, the drawing direction being either a direction of rotation of the pair of gear rolls or a direction parallel to the axes of rotation,
each gear roll of the pair of gear rolls has the plurality of teeth arranged at an arrangement pitch in the drawing direction,
the plurality of recessed sections in the raw sheet includes a plurality of rows of recessed sections, each row among the plurality of rows including a number of the recessed sections arranged collinearly along the drawing direction, the plurality of rows being arranged side-by-side in a direction orthogonal to the drawing direction,
in the respective plurality of rows of recessed sections, the plurality of recessed sections is formed at respective predetermined formation pitches along the drawing direction,
with respect to each row among the plurality of rows of the plurality of recessed sections in the raw sheet, the arrangement pitch of the teeth in the drawing direction is configured to be greater than the respective formation pitch in said each row of the plurality of rows and smaller than twice the respective formation pitch in said each row,
the plurality of rows of recessed sections includes
a first row of recessed sections having the respective formation pitch of a first predetermined value, and
a second row of recessed sections having the respective formation pitch of a second predetermined value,
the first predetermined value and the second predetermined value are different from each other,
the arrangement pitch of the plurality of teeth in the drawing direction is configured to be greater than the first predetermined value and smaller than twice the first predetermined value, and the arrangement pitch of the plurality of teeth in the drawing direction is configured to be greater than the second predetermined value and smaller than twice the second predetermined value.

2. An apparatus configured to produce a stretchable sheet, the apparatus comprising:
a forming section configured to form a plurality of recessed sections in a raw sheet by pressing the raw sheet, the recessed sections being formed collinearly at least along a drawing direction at a predetermined formation pitch in the drawing direction;
a pair of gear rolls; and
a supply section configured to supply the raw sheet having the plurality of recessed sections to the pair of gear rolls,
wherein
each gear roll of the pair of gear rolls has a plurality of teeth arranged on a circumference thereof, the pair of gear rolls being rotatable about respective axes of rotation with the plurality of teeth meshing each other,
the plurality of teeth of the pair of gear rolls is configured to draw the raw sheet, on which the plurality of recessed sections has been formed, in the drawing direction by passing the raw sheet through a gap between the pair of gear rolls, the raw sheet containing a plurality of types of fibers, the drawing direction being either a direction of rotation of the pair of gear rolls or a direction parallel to the axes of rotation,
with respect to each gear roll of the pair of gear rolls, an arrangement pitch of the teeth in the drawing direction is configured to be greater than the predetermined formation pitch and smaller than twice the predetermined formation pitch,
the plurality of recessed sections of the raw sheet forms a plurality of rows of recessed sections in a direction orthogonal to the drawing direction, the plurality of rows of recessed sections being arranged side-by-side at a pitch in the drawing direction, and the arrangement pitch of the plurality of teeth in the drawing direction is configured to be greater than the pitch of the plurality of rows and smaller than twice the pitch of the plurality of rows.

3. The apparatus according to claim 1, wherein the drawing direction is the direction of rotation of the pair of gear rolls.

4. The apparatus according to claim 1, wherein the drawing direction is the direction parallel to the axes of rotation.

5. The apparatus according to claim 1, wherein the pair of gear rolls is configured such that a single recessed section among the plurality of recessed sections on the raw sheet is placed between a tooth of one of the pair of gear rolls and a corresponding tooth of the other one of the pair of gear rolls when passing the raw sheet through the gap between the pair of gear rolls.

6. The apparatus according to claim 1, wherein the pair of gear rolls is configured such that the recessed sections among the plurality of recessed sections is placed offset from the teeth of the pair of gear rolls when passing the raw sheet through the gap between the pair of gear rolls.

7. The apparatus according to claim 2, wherein the drawing direction is the direction of rotation of the pair of gear rolls.

8. The apparatus according to claim 2, wherein the drawing direction is the direction parallel to the axes of rotation.

9. The apparatus according to claim 2, wherein the pair of gear rolls is configured such that a single recessed section among the plurality of recessed sections on the raw sheet is placed between a tooth of one of the pair of gear rolls and a corresponding tooth of the other one of the pair of gear rolls when passing the raw sheet through the gap between the pair of gear rolls.

10. The apparatus according to claim 2, wherein the pair of gear rolls is configured such that the recessed sections among the plurality of recessed sections is placed offset from the teeth of the pair of gear rolls when passing the raw sheet through the gap between the pair of gear rolls.

* * * * *